United States Patent [19]
Ruddy et al.

[11] Patent Number: 5,593,657
[45] Date of Patent: Jan. 14, 1997

[54] BARIUM SALT FORMULATIONS STABILIZED BY NON-IONIC AND ANIONIC STABILIZERS

[75] Inventors: Stephen B. Ruddy, Schwenkville; W. Mark Eickhoff, Downingtown; Gary Liversidge, West Chester; Mary E. Roberts, Downingtown, all of Pa.

[73] Assignee: NanoSystems L.L.C., Collegeville, Pa.

[21] Appl. No.: 386,027

[22] Filed: Feb. 9, 1995

[51] Int. Cl.⁶ .................................................. A61K 49/04
[52] U.S. Cl. ...................... 424/9.41; 514/57; 514/717; 514/941; 424/9.411
[58] Field of Search ................ 424/5; 514/57, 514/717, 941

[56] References Cited

U.S. PATENT DOCUMENTS

| | | | |
|---|---|---|---|
| 2,680,087 | 6/1954 | Lowy | 167/95 |
| 2,689,690 | 9/1954 | Dudchik | 242/55 |
| 3,216,900 | 11/1965 | Embring et al. | 167/95 |
| 3,235,462 | 2/1966 | Wolfson | 167/95 |
| 4,038,379 | 7/1977 | Elinov et al. | 424/4 |
| 4,120,946 | 10/1978 | Queuille et al. | 424/4 |
| 5,310,538 | 5/1994 | Bacon et al. | 424/5 |

FOREIGN PATENT DOCUMENTS

0498482A2  1/1992  European Pat. Off. ........ A61K 49/04

OTHER PUBLICATIONS

"Pharmaceuticals in Medical Imaging" by Swanson et al, 1990.

*Primary Examiner*—Paul J. Killos
*Attorney, Agent, or Firm*—Rudman & Balogh

[57] ABSTRACT

Disclosed are x-ray contrast compositions for oral or retrograde examination of the gastrointestinal tract comprising nanoparticles of a barium salt having associated with its surface non-ionic and anionic stabilizers; and methods for their use in diagnostic radiology of the gastrointestinal tract.

22 Claims, No Drawings

BARIUM SALT FORMULATIONS STABILIZED BY NON-IONIC AND ANIONIC STABILIZERS

FIELD OF INVENTION

This invention relates to an x-ray contrast composition for oral or retrograde administration to a mammal comprising a nanoparticulate barium salt stabilized by a combination of non-ionic and anionic stabilizers as the contrast producing agent in a pharmaceutically acceptable carrier.

BACKGROUND OF THE INVENTION

Roentgenographic examination utilizing x-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate x-ray radiation. D. P. Swanson et al in "Pharmaceuticals In Medical Imaging", 1990, MacMillan Publishing Company, provides an excellent background in medical imaging utilizing contrast agents and compositions therewith.

The desiderata for an ideal GI contrast agent includes: good toxicological profile; the ability to fill the entire bowel/lumen and evenly coat the gut mucosa so that the presence of the bowel is detectable when the lumen is not distended; palatability and non irritation to the intestinal mucosa; and passing through the GI tract without producing artifacts or stimulating vigorous intestinal peristalsis.

The most widely used contrast agents for the visualization of the GI tract is barium sulfate administered as a suspension orally or rectally as an enema. (See for example, U.S. Pat. Nos. 2,659,690; 2,680,089; 3,216,900; 3,235,462; 4,038,379 and 4,120,946.) Notwithstanding its relatively good contrast characteristics, negligible absorption from the GI tract following oral or rectal administration and speedy excretion from the body, barium sulfate has certain disadvantages. In the presence of intestinal fluids, it lacks homogeneity which can result in poor x-ray images. In the colon, when administered as an enema, it flocculates and forms irregular clumps with fecal matter. The prior art considers as a serious problem the difficulty in achieving uniform adherence to, and coating of, the mucosa of the GI tract by the water insoluble barium sulfate to provide high quality x-ray photographs. As a result of inadequate adherence to, and non-uniform coating of the mucosa, the x-ray results are often inferior, misleading to the practitioner and the imaging process must be repeated. It has also been observed that the barium sulfate, and other solid inorganic particulate radiopaque agents tend to settle out in the patient after evacuation but before and during x-ray imaging, which again deleteriously affects the quality of the x-ray pictures.

These drawbacks were addressed by many investigators and their efforts resulted in great improvements over the years. However, the drawbacks of uneven coating of the mucosa by an x-ray contrast composition and insufficient adherence to the mucosa has proven to be rather difficult to solve.

While some advancements have been made which enhance attachment of the contrast agents to the walls of organs for better visualization thereof, there is still a need for an improved x-ray imaging medium that uniformly coats the soft tissues subjected to diagnostic x-ray examination.

We have now discovered that good adherence to, and uniform coating of the mucosa of the intestine can be obtained by a nanoparticulate barium salt stabilized by a combination of a primary nonionic and a secondary anionic stabilizer.

It is the object of the present invention to provide compositions for coating the gastrointestinal tract of mammals to form an effective radiopaque coating thereon by which diagnostic examination of the GI tract may be accomplished.

SUMMARY OF INVENTION

The object of the present invention is achieved by a composition of matter comprising a suspension of a nanoparticulate barium salt stabilized by having associated with its surface a combination of a non-ionic and an anionic stabilizer in a pharmaceutically acceptable vehicle used as a x-ray contrast agent.

Preferably, the composition of matter comprises an aqueous suspension of barium sulfate particles having a mean number average particle size of less than about 1 micron having associated with its surface a polyethylene oxide-polypropylene oxide tri-block copolymer and an anionic alkyl sulfate.

In a preferred embodiment the composition of matter comprises an aqueous suspension of barium sulfate particles of a mean number average particle size of less than about 1 micron, a primary non-ionic stabilizer being a tri-block copolymer of polyethylene oxide and polypropylene oxide, and a secondary anionic stabilizer being sodium dodecyl sulfate.

In an even more preferred embodiment the composition of matter comprises an aqueous suspension of 15–25% w/v barium sulfate particles of a mean number average particle size of less than about 1 micron; a primary non-ionic stabilizer being 4.0–6.0% w/v of a block copolymer of polyethylene oxide and polypropylene oxide, or 1.0–2.5% w/v of hydroxypropyl methyl cellulose; 0.05–0.2% w/v of a secondary anionic stabilizer being sodium dodecyl sulfate and the balance water.

These compositions provide improved gastrointestinal imaging when they are used in a method of carrying out x-ray examination of the gastrointestinal tract of a patient. The method comprises the oral or rectal administration to the patient of an x-ray contrast formulation of the compositions of the present invention.

DETAILED DESCRIPTION OF THE INVENTION

The present invention comprises novel formulations of barium salts in which the individual barium salt particles are surface stabilized by a combination of stabilizers.

The preferred barium salt utilized in the present invention is barium sulfate which is a white, radiopaque, crystalline powder that is essentially insoluble in water. However, good results are obtainable with other inorganic, essentially water-insoluble salts of barium including barium hexaboride, barium chromite, barium fluogallate, barium tri-ortho phosphate, barium metasilicate, barium titanate, barium zirconate and zirconium oxide. The compositions of the present invention contain from about 1%—about 99% w/v, preferably 10–40% w/v, most preferably 15–25% w/v, of the barium salt. The compositions may be in the form of dispersions, colloids or suspensoids.

The primary stabilizers are nonionic. The nonionic stabilizers employed are believed to possess "bioadhesive" or "mucoadhesive" properties. These effects of which are unexpectedly and unobviously augmented significantly by the presence of an anionic stabilizer.

Nonionic surface stabilizers useful in the invention include: cellulose-based polymers such as methyl cellulose, hydroxypropyl cellulose and hydroxypropyl methyl cellulose (such as Methocel K4M—sold by the Dow Chemical Company), carboxylic esters (such as sorbitan esters) and ethoxylated derivatives, carboxylic amides, ethoxylated alkylphenols and ethoxylated alcohols, ethylene oxide/propylene oxide copolymers (such as poloxamer 407, 188, 237 and 338, and other poloxamer polymers such as those sold by BASF under the trademark Pluronic), polyvinyl pyrrolidone and polyvinyl alcohol.

Preferred are hydroxypropyl methyl cellulose and ethylene oxide/propylene oxide tri-block copolymers.

The compositions of the present invention comprise nonionic stabilizer in the range of 0.25–25% w/v, preferably 1.0–10% w/v, most preferably 4.0–6.0% w/v.

The secondary stabilizer is an anionic stabilizer including zwitterionic stabilizers which possess a net negative charge at physiologically relevant pH.

Suitable anionic stabilizers include sodium alkyl sulfates (such as sodium dodecyl sulfate) and related salts, alkyl benzenesulfonic acids and salts thereof, butyl naphthalene sulfonates and sulfosuccinates.

The compositions of the present invention comprise an anionic stabilizer in the range of 0.001–5% w/v, preferably 0.01–0.5% w/v, most preferably 0.05–0.2% w/v.

As used herein nanoparticle means that the stabilized barium salt has a mean number average particle size of less than about 1 micron, preferably less than 400 nanometers.

One method of determining the mean average particle size is dynamic laser light scattering.

Barium sulfate is commercially available in a broad range of particle sizes. Commercial products generally contain material ranging from 400 nanometers to 10 microns and has an mean average diameter of 2 microns. These particles may be individual particles or aggregates of smaller particles.

The commercially available barium salts are formulated into nanoparticulate x-ray contrast agents useful in the present invention by various methods known in the art, such as wet milling, microfluidization, fluid air jet milling, high-shear mixing and controlled precipitation.

The stabilized barium salt is formulated for administration using physiologically acceptable carriers or excipients in a manner within the skill of the art. The barium salt and the combination of stabilizers, with the addition of pharmaceutically acceptable aids and excipients are suspended in an aqueous medium resulting in a dispersion or suspension.

A method for diagnostic imaging of the GI tract for use in medical procedures in accordance with this invention comprises orally or rectally administering to the mammalian patient in need of an x-ray examination, an effective contrast producing amount of a composition of the present invention. After administration at least a portion of the GI tract containing the administered composition is exposed to x-rays to produce an x-ray image pattern corresponding to the presence of the contrast agent, then the x-ray image is visualized and interpreted using techniques known in the art.

The resulting barium formulations provide for extensive and uniform coating of major portions of the GI tract.

The percentages of the principal components of the compositions of the present invention are as follows:

| Ingredient | Barium salts | Nonionic SAA | Ionic SAA |
| --- | --- | --- | --- |
| Broad range (% w/v) | 1–99 | 0.25–25 | 0.001–5 |
| Preferred range (% w/v) | 10–40 | 2.5–10 | 0.01–0.5 |
| Most preferred range (% w/v) | 15–25 | 4.0–6.0 | 0.05–0.2 |
| Water q.s. to 100% by volume | | | |

Additional ingredients known to these skilled in the art may also be included. Ingredients routinely employed in pharmaceutical suspensions include sweetening and flavoring agents (such as saccharine sodium), colors, lakes, dyes, antifoam agents (such as simethicone), preservatives (such as parabens or benzoic and sorbic acids) and viscosity enhancers.

The aqueous vehicle ultimately is to contain a combination of stabilizers and additional excipients.

The order of addition prior to mixing is unimportant, provided that the individual barium particles are ultimately wetted. The contents are then subjected to a mixing or blending process sufficient to disperse the materials uniformly throughout the product.

Alternatively, the formulations may be prepared by methods other than direct incorporation (such as controlled precipitation of, for example, barium sulfate from soluble barium salts).

One method of preparing nanoparticles useful in the present invention is in accordance with the wet grinding process described in EPO498,482, the disclosure of which is hereby incorporated by reference in its entirety. The process comprises dispersing a poorly soluble barium salt in a liquid dispersion medium and wet-grinding the agent in the presence of grinding media to reduce the particle size of the contrast agent to an effective mean number average particle size of less than about 400 nm. The particles can be reduced in size in the presence of stabilizers. Alternatively, the particles can be contacted with the stabilizers after attrition.

A general procedure for preparing the particles useful in the practice of this invention follows. The barium salt selected is obtained commercially and/or prepared by techniques known in the art as described above, in a conventional coarse form. It is preferred, but not essential, that the particle size of the coarse barium salt selected be less than about 100 microns as determined by sieve analysis. If the coarse particle size of the contrast agent is greater than about 100 microns, then it is preferred that the coarse particles of the barium salt be reduced in size to less than 100 microns using a conventional milling method such as airjet or fragmentation milling.

The coarse barium salt selected can then be added to a liquid medium in which it is essentially insoluble to form a premix. It is preferred, but not essential, that the stabilizers be present in the premix.

The premix can be used directly by wet grinding to reduce the mean number average particle size in the dispersion to less 1 micron, preferably less than 400 nm. It is preferred that the premix be used directly when a ball mill is used for attrition. Alternatively, the barium salt and, optionally, the stabilizers, can be dispersed in the liquid medium using suitable agitation, e.g., a roller mill or a Cowles type mixer, until a homogeneous dispersion is achieved. It is preferred that the premix be subjected to such a premilling dispersion step when a recirculating media mill is used for attrition.

Wet grinding can take place in any suitable dispersion mill, including, for example, a ball mill, an attritor mill, a vibratory mill, and media mills such as a sand mill and a bead mill. A media mill is preferred due to the relatively shorter milling time required to provide the intended result, i.e., the desired reduction in particle size. For media milling, the apparent viscosity of the premix preferably is from about 100 to about 1000 centipoise. For ball milling, the apparent viscosity of the premix preferably is from about 1 up to about 100 centipoise. Such ranges tend to afford an optimal balance between efficient particle fragmentation and media erosion.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of material for the grinding media is not believed to be critical. However, preferred media have a density greater than about 3 g/cm³. We have found that zirconium oxide, such as 95% ZrO stabilized with magnesia, zirconium silicate, and glass grinding media provide particles having levels of contamination which are believed to be acceptable for the preparation of x-ray contrast compositions. However, other media, such as stainless steel, titania, alumina, and 95% ZrO stabilized with yttrium, are believed to be useful.

The attrition time can vary widely and depends primarily upon the particular wet grinding mill selected. For ball mills, processing times of up to five days or longer may be required. On the other hand, processing times of less than 1 day (residence times of about one minute up to several hours) have provided the desired results using a high shear media mill.

The particles must be reduced in size at a temperature which does not significantly degrade the barium salt. Processing temperatures of less than about 30°–40° C. are ordinarily preferred. If desired, the processing equipment can be cooled with conventional cooling equipment. The method is conveniently carried out under conditions of ambient temperature and at processing pressures which are safe and effective for the milling process. For example, ambient processing pressures are typical of ball mills, attritor mills and vibratory mills. Processing pressures up to about 20 psi (1.4 kg/cm²) are typical of media milling.

The stabilizers, if not present in the premix, must be added to the dispersion after attrition in an amount as described for the premix. Thereafter, the dispersion can be mixed, e.g., by shaking vigorously. Optionally, the dispersion can be subjected to a sonication step, e.g., using an ultrasonic power supply. For example, the dispersion can be subjected to ultrasonic energy having a frequency of 20–80 kHz for a time of about 1 to 120 seconds.

The compositions of the invention may be administered orally to the patient for radiological examination of the GI tract. The compositions of the invention may also be administered rectally in the form of enemas to a patient for radiologic examination of the colon.

The compositions of the present invention possess very good adherence to the walls of the gastrointestinal tract by forming an essentially uniform coating thereon.

The invention having been fully described, it will be apparent to one skilled in the art that changes and modifications can be made thereto without departing from the spirit and scope thereof.

The following examples further illustrate the invention.

EXAMPLES

Example 1

| | |
|---|---|
| 15.0% | Barium Sulfate, U.S.P. |
| 1.5% | hydroxypropyl methylcellulose (HPMC) |
| 0.1% | sodium dodecyl sulfate (SDS) |
| 0.1% | simethicone emulsion |
| 0.1% | saccharine sodium |
| 0.1% | natural orange flavor |
| 0.1% | FD & C red dyes |
| Purified water q.s. to volume | |

Example 2

| | |
|---|---|
| 25.0% | Barium Sulfate, U.S.P. |
| 5.0% | poloxamer 188 a copolymer of ethylene oxide/propylene oxide |
| 0.1% | sodium dodecyl sulfate |
| 5.0% | sorbitol |
| 0.1% | natural strawberry flavor |
| 0.1% | natural banana flavor |
| 0.1% | FD & C red dyes |
| 0.1% | FD & C yellow dyes |
| Purified water q.s. to volume | |

Example 3

| | |
|---|---|
| 22.0% | Barium Sulfate, U.S.P. |
| 3.5% | polyvinyl pyrrolidone |
| 0.2% | dioctyl sodium sulfosuccinate |
| 2.0% | xylitol |
| 0.1% | saccharine sodium |
| 0.1% | sodium benzoate |
| 0.1% | sodium sorbate |
| 0.1% | imitation vanilla flavor |
| Purified water q.s. to volume | |

COMPARATIVE EXAMPLES 1–2

The following results were obtained in radiographic examination of the GI tracts of beagle dogs following the oral administration (10 mL/kg) of various barium sulfate formulations.

Formulations used in Comparative Example 1 contained 10% w/v barium sulfate.

Formulations used in Comparative Example 2 contained 15% w/v barium sulfate.

The in vivo performance of various barium sulfate formulations was evaluated in beagle dogs according to the following procedure.

Animals were initially sedated with an appropriate dose of acepromazine (selected because it exhibits no unwanted effects of GI motility).

Animals were then dosed (10 mL/kg) with the test article via gastric tube. At 15 or 30 minutes post-administration, an equivalent volume of air was administered to simulate a double-contrast effect.

Dogs were studied in the dorsal recumbent position, resulting in ventral-dorsal x-ray exposure of the abdominal cavity. Radiographs were generated at 15, 30, 45, 60, 120 and 240 minutes post-administration, after which each was developed and reviewed.

In order to compare radiographs and to assess differences in image quality among various formulations, a grading scheme was assembled as follows:

0 little to no evidence of mucosal coating; excessive radiopacity predominates 1 limited mucosal coating observed; excessive radiopacity is evident 2 mucosal coating observed over 50% of small intestine
3 2+mucosal coating persists for at least 30 minutes
4 3+mucosal coating results in transradiation of multiple bowel loops
5 4+mucosal coating results in moderate to high level of surface detail
6 5+mucosal coating observed at later timepoints (1 hr or later) reveals limited evidence of physical incompatibility arising from GI fluid
7 6+overall image is sharp and crisp; high diagnostic potential for brush-border abnormalities and small surface lesions

COMPARATIVE EXAMPLE 1

| Surface Stabilizer | Grade | Overall Image Quality Diagnostic Value |
|---|---|---|
| no stabilizer | 0 | poor/nondiagnostic |
| 0.1% SDS | 0 | poor/nondiagnostic |
| 4% Pluronic F127 | 4 | good/diagnostic |
| 4% Pluronic F127 and 0.1% SDS | 6 | excellent/diagnostic |

COMPARATIVE EXAMPLE 2

| Surface Stabilizer(s) | Grade | Overall Image Quality/ Diagnostic Value |
|---|---|---|
| no stabilizer | 0 | poor/nondiagnostic |
| 0.1% SDS | 0 | poor/nondiagnostic |
| 1.5% HPMC | 5 | good/diagnostic |
| 1.5% HPMC + 0.1% SDS | 7 | excellent/diagnostic |

COMPARATIVE EXAMPLE 3

A series of experiments were conducted to ascertain the particle size obtained and the physical stability of the obtained nanoparticles in intestinal fluid. All the compositions tested were comprised of 15% w/v of barium sulfate, 4.0% w/v of the designated non-ionic stabilizer and 0.1% w/v of the ionic stabilizer (if used).

All the compositions were made by ballmilling the mixture of the components for 2–4 days.

The following were the results:

Formulations: Pluronic Series

Pluronic polymers are stabilizers which are sold by BASF. They are made by the controlled addition of propylene oxide to the two hydroxyl groups of propylene glycol. Then ethylene oxide is added to sandwich this hydrophobe between hydrophilic groups. The reaction is controlled to obtain polymers of a desired molecular weight and percentage of hydrophile.

SDS is sodium dodecyl sulfate—an anionic stabilizer.

CTAB is cetyl trimethylammonium bromide—a cationic compound.

| Formulation | Nonionic Stabilizer | Anionic Stabilizer or Cationic Compound | Particle Size (nm) mean (90th percentile) | Physical Stability in Intestinal Fluids (min)[a] |
|---|---|---|---|---|
| 102A1 | Pluronic F68 | — | 279 (320) | 35 |
| 102A2 | Pluronic F68 | SDS | 225 (360) | 150 |
| 102A3 | Pluronic F68 | CTAB | 287 (414) | 10 |
| 102E1 | Pluronic F77 | — | 252 (353) | 35 |
| 102E2 | Pluronic F77 | SDS | 214 (302) | 130 |
| 102E3 | Pluronic F77 | CTAB | 29 (383) | 15 |
| 102F1 | Pluronic F87 | — | 256 (367) | 40 |
| 102F2 | Pluronic F87 | SDS | 225 (322) | 200 |
| 102F3 | Pluronic F87 | CTAB | 343 (528) | 20 |
| 102B1 | Pluronic F88 | — | 305 (604) | 20 |
| 102B2 | Pluronic F88 | SDS | 202 (283) | 280 |
| 102B3 | Pluronic F88 | CTAB | 322 (405) | 35 |
| 102C1 | Pluronic F98 | — | 261 (320) | 35 |
| 102C2 | Pluronic F98 | SDS | 232 (297) | 325 |
| 102C3 | Pluronic F98 | CTAB | 428 (483) | 30 |
| 102D1 | Pluronic F108 | — | 253 (360) | 40 |
| 102D2 | Pluronic F108 | SDS | 43 (74) | 590 |
| 102D3 | Pluronic F108 | CTAB | 326 (499) | 70 |
| 102G1 | Pluronic F127 | — | 249 (330) | 45 |
| 102G2 | Pluronic F127 | SDS | 342 (455) | 510 |
| 102G3 | Pluronic F127 | CTAB | 328 (478) | 30 |

Formulations: Tetronic Series

Tetronic polymer are sold by BASF. They are tetrafunctional block copolymers derived from the sequential addition of propylene oxide and ethylene oxide to ethylediamine.

| Formulation | Nonionic Stabilizer | Anionic Stabilizer or Cationic Compound | Particle Size (nm) mean (90th percentile) | Physical Stability in Intestinal Fluids (min)[a] |
|---|---|---|---|---|
| 102O1 | Tetronic 908 | — | 277 (387) | 45 |
| 102O2 | Tetronic 908 | SDS | 212 (302) | 665 |
| 102O3 | Tetronic 908 | CTAB | 329 (483) | 20 |
| 102R1 | Tetronic 1107 | — | 230 (309) | 45 |
| 102R2 | Tetronic 1107 | SDS | 214 (287) | 55 |
| 102R3 | Tetronic 1107 | CTAB | 279 (358) | 40 |
| 102S1 | Tetronic 1307 | — | 276 (348) | 45 |
| 102S2 | Tetronic 1307 | SDS | 232 (337) | 515 |
| 102S3 | Tetronic 1307 | CTAB | 344 (512) | 35 |

Formulations: Misc Stabilizers

PEG is poly ethylene glycol

PVA is poly vinyl alcohol

PVP is poly vinyl pyrrolidone

Polysorbate 80 is polyoxyethylene (20) sorbitan monooleate

| Formulation | Nonionic Compound | Anionic Stabilizer or Cationic Compound | Particle Size (nm) mean (90th percentile) | | Physical Stability in Intestinal Fluids[d] (min)[a] |
|---|---|---|---|---|---|
| 102H1 | Tyloxapol | — | 258 | (371) | 20 |
| 102H2 | Tyloxapol | SDS | 285 | (396) | 35 |
| 102H3 | Tyloxapol | CTAB | 280 | (400) | 25 |
| 102I1 | PVA | — | 307 | (405) | 45 |
| 102I2 | PVA | SDS | 210 | (381) | 720 |
| 102I3 | PVA | CTAB | 334 | (424) | 20 |
| 102J1 | PVP | — | 291 | (398) | 40 |
| 102J2 | PVP | SDS | 291 | (354) | ND |
| 102J3 | PVP | CTAB | 349 | (591) | 10 |
| 102K1 | Polysorbate 80 | — | 261 | (383) | 25 |
| 102K2 | Polysorbate 80 | SDS | 256 | (422) | 80 |
| 102K3 | Polysorbate 80 | CTAB | 322 | (504) | 30 |
| 102L1 | PEG 400 | — | 274 | (457) | 35 |
| 102L2 | PEG 400 | SDS | ND | | ND |
| 102L3 | PEG 400 | CTAB | 294 | (402) | 15 |
| 102M1 | PEG 1450 | — | 277 | (327) | 35 |
| 102M2 | PEG 1450 | SDS | ND | | ND |
| 102M3 | PEG 1450 | CTAB | 302 | (419) | 10 |
| 102N1 | PEG 4000 | — | 266 | (365) | 40 |
| 102N2 | PEG 4000 | SDS | ND | | ND |
| 102N3 | PEG 4000 | CTAB | 342 | (490) | 10 |
| 102U1 | PEG 18500 | — | 265 | (344) | 40 |
| 102U2 | PEG 18500 | SDS | 44 | (77) | 720 |
| 102U3 | PEG 18500 | CTAB | 386 | (703) | 60 |

[a]Time required to reach 50% of initial absorbance following a 1:100 (v/v) dilution in Simulated Intestinal Fluid, U.S.P.

Physical stability of nanoparticulate dispersions in the presence of Simulated Intestinal Fluid USP was assessed by:

a/Particle Size Measurements

Measurements were made using low angle laser light scattering (LALLS). Samples were diluted 1:1 in simulated intestinal fluid (SIF) or Water (control), mixed well by vortexing (10 sec) and allowed to sit undisturbed for at least 1 hour at room temperature. Effective particle sizes following incubation were measured using water as the medium. Assumption: Instability in the presence of simulated fluids will be evidenced by an increase in effective particle size indicating severe aggregate formation.

b/Spectrophotometric Turbidity Measurements

Physical stability of dispersions was assessed spectrophotometrically. Dispersions were diluted 1:100 in SIF, or 0.1% SDS as a control. Absorbance was monitored at 600 nm using 1 mL disposable cuvettes for up to 12 hours with data points collected at five minute intervals.

Assumption: Instability in the presence of simulated fluids will be evidenced by a decrease in absorbance over time. This decrease in absorbance is indicative of the formation of aggregates in the test sample which settle out over time.

These results indicate that the smaller particle size and greater stability are the reason that enhanced GI imaging is observed when compositions of the present invention are utilized.

The invention has been described in detail with particular reference to certain preferred embodiments thereof, but it will be understood that variations and modifications can be effected within the spirit and scope of the invention.

What is claimed is:

1. A composition of matter, free of iodinated compounds, comprising: nanoparticles of a barium salt having associated with the surface thereof a combination of a non-ionic and an anionic stabilizer.

2. The composition of claim 1 wherein the barium salt is barium sulfate, barium hexaboride, barium chromate, barium fluogallate, barium tri-ortho phosphate, barium metasilicate, barium titanate, barium zirconate and zirconium oxide.

3. The composition of claim 2 wherein the barium salt is barium sulfate.

4. The composition of claim 1 wherein the barium salt is present in the composition in a range of 1%—about 99% w/v.

5. The composition of claim 1 wherein the barium salt is present in the composition in a range of 10–40% w/v.

6. The composition of claim 1 wherein the barium salt is present in the composition in a range of 15–25% w/v.

7. The composition of claim 1 wherein the non-ionic stabilizer is the major component of the combination.

8. The composition of claim 1 wherein the non-ionic stabilizer is methyl cellulose, hydroxypropyl cellulose, hydroxypropyl methyl cellulose, carboxylic esters and ethoxylated derivatives, carboxylic amides, ethoxylated alkylphenols, ethoxylated alcohols, ethylene oxide/propylene oxide copolymers, polyvinyl pyrrolidone or polyvinyl alcohol.

9. The composition of claim 8 wherein the non-ionic stabilizer is hydroxypropyl methyl cellulose or an ethylene oxide/propylene oxide tri-block copolymer.

10. The composition of claim 1 wherein the nonionic stabilizer is in the range of 0.25–25% w/v.

11. The composition of claim 1 wherein the nonionic stabilizer is in the range of 1.0–10% w/v.

12. The composition of claim 1 wherein the nonionic stabilizer is in the range of 4.0–6.0% w/v.

13. The composition of claim 1 wherein the anionic stabilizer is selected from the group comprising sodium alkyl sulfates and related salts, alkyl benzenesulfonic acids and salts thereof, or butyl naphthalene sulfonates and sulfosuccinates.

14. The composition of claim 13 wherein the anionic stabilizer is sodium dodecyl sulfate.

15. The composition of claim 1 wherein the anionic stabilizer is in the range of 0.001–5% w/v.

16. The composition of claim 1 wherein the anionic stabilizer is in the range of 0.01–0.5% w/v.

17. The composition of claim 1 wherein the anionic stabilizer is in the range of 0.05–0.2% w/v.

18. A composition of matter, free of iodinated compounds, comprising:
an aqueous suspension of barium sulfate particles having a mean number average particle size of less than about 1 micron having associated with its surface a non-ionic stabilizer being polyethylene oxide-polypropylene oxide tri-block copolymer or hydropropyl methyl cellulose; and an anionic alkyl sulfate.

19. A composition of matter, free of iodinated compounds, useful as an x-ray contrast agent for GI tract, the composition comprising
an aqueous suspension of barium sulfate particles of a mean number average particle size of less than about 1 micron,
a primary non-ionic stabilizer being a tri-block copolymer of polyethylene oxide and polypropylene oxide or hydroxypropyl methyl cellulose, and
a secondary anionic stabilizer being sodium dodecyl sulfate.

20. A composition of matter, free of iodinated compounds, useful as an x-ray contrast agent for GI tract, the composition comprising an aqueous suspension of

- 15–25% w/v barium sulfate particles of a mean number average particle size of less than about 1 micron,
- 4.0–6.0% w/v of a primary non-ionic stabilizer being a block copolymer of polyethylene oxide and polypropylene oxide,
- 0.1–0.2% w/v of a secondary anionic stabilizer being sodium dodecyl sulfate and the balance water.

21. A composition of matter, free of iodinated compounds, useful as an x-ray contrast agent for GI tract, the composition comprising
an aqueous suspension of

- 15–25% w/v barium sulfate particles of a mean number average particle size of less than about 1 micron,
- 1.0–2.5% w/v of a primary non-ionic stabilizer being a hydroxypropyl methyl cellulose,
- 0.1–0.2% w/v of a secondary anionic stabilizer being sodium dodecyl sulfate and the balance water.

22. The method of carrying out x-ray examination of the gastrointestinal tract of a patient, said method comprises the oral or rectal administration to the patient an x-ray contrast formulation comprising:

the composition of claim 1.

* * * * *